United States Patent [19]

Hansen

[11] Patent Number: 4,950,159

[45] Date of Patent: Aug. 21, 1990

[54] FILTER CARTRIDGE FOR DENTAL SYRINGE

[76] Inventor: James W. Hansen, 34 Mint Cir., Middleburg, Fla. 32068

[21] Appl. No.: 399,012

[22] Filed: Aug. 28, 1989

[51] Int. Cl.$^5$ ............................................. A61G 17/02
[52] U.S. Cl. ..................................................... 433/80
[58] Field of Search ....................... 433/80, 81, 82, 84, 433/85, 87, 88

[56] References Cited

U.S. PATENT DOCUMENTS 4,249,899  2/1981  Davis ...................................... 433/80
4,741,697  5/1988  Herbison ................................ 433/25

FOREIGN PATENT DOCUMENTS 1061959  8/1956  Fed. Rep. of Germany ........ 433/80

Primary Examiner—John J. Wilson
Attorney, Agent, or Firm—Arthur G. Yeager

[57] ABSTRACT

Filter cartridge for filtering air and water dispersed by a dental syringe; the cartridge being a cylindrical member divided into two lengthwise spaces, one filled with water filtering material and the other filled with air filtering material; the cartridge having a barbed prong coupler from each lengthwise space for coupling to a flexible hose support for air or water, respectively; the cartridge having two female recesses for joining each of the two lengthwise spacers separately to barbed prong couplers on the dental syringe.

9 Claims, 2 Drawing Sheets

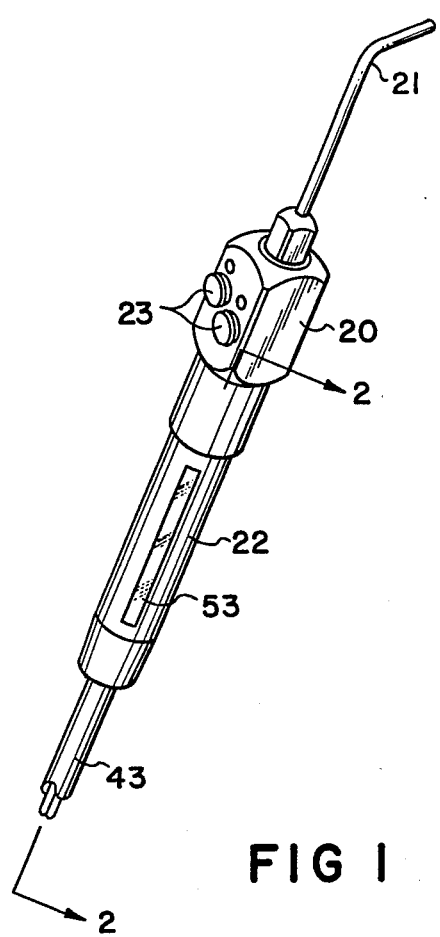
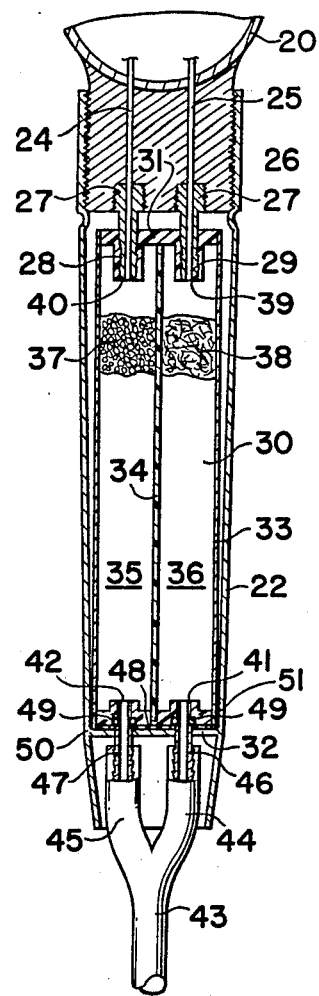
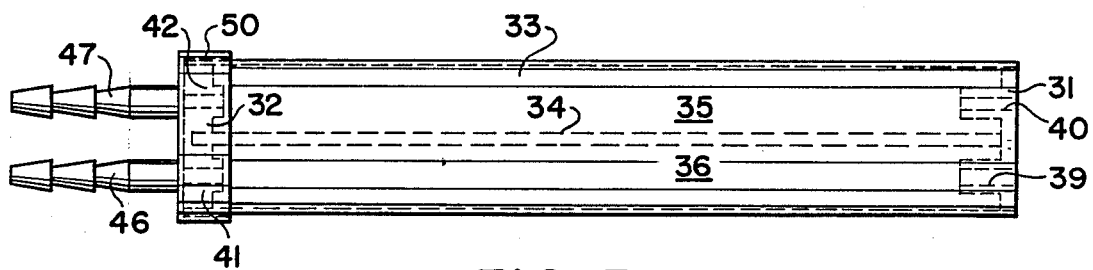
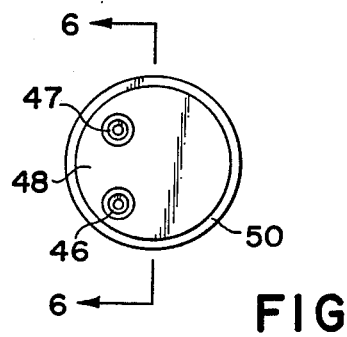
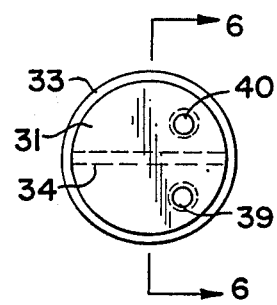
FIG 1
FIG 2
FIG 3
FIG 4
FIG 5

FILTER CARTRIDGE FOR DENTAL SYRINGE

BACKGROUND OF THE INVENTION

It is well known that one of the dentists instruments is a syringe which has an elongated spout or nozzle which can be directed into the patient's mouth to deliver selectively a small stream of water or a small stream of air to any location in the mouth and around the teeth and gums of the patient. This instrument is connected by a twin conduit flexible hose (one conduit for water and the other conduit for air) to sources of pressurized water and pressurized air. Unless the water source and the air source have individual filtering means, the water and air delivered from the nozzle of the syringe are not filtered so as to be free of dirt, particles, and other contaminants.

It is an object of this invention to provide a small filter cartridge for filtering the air and water separately. It is another object of this invention to provide a disposable filter cartridge for filtering air and water dispensed by a dental syringe wherein the filter cartridge is concealed in the handle of the syringe. Still other objects will become apparent from the more detailed description of this invention which follows.

BRIEF SUMMARY OF THE INVENTION

This invention relates to a dental syringe for selectively directing streams of air or water into a patient's mouth, having a disposable filter cartridge with separate filters for air and for water comprising:

(a) an elongated cartridge body having a forward wall, a rearward wall, and a side wall enclosing an internal space divided into two longitudinal half spaces by an internal axial wall extending from said forward wall to said rearward wall; the first of said longitudinal spaces being filled with water filtering material and the second of said spaces being filled with air filtering material; an entrance passageway for water through said rearward wall into said first space, an entrance passageway for air through said rearward wall into said second space; an exit passageway from said first space through said forward wall to a coupling means with said syringe; and exit passageway from said second space through said forward wall to a coupling means with said syringe; and means to couple said entrance passageways to separate sources of pressurized air and pressurized water.

In specific and preferred embodiments of the invention the water filtering material is activated charcoal and the air filtering means is cotton fleece; the coupling means between the syringe and the filter cartridge and between the filter cartridge and sources of pressurized water and air are combinations of tubular barbed prongs and recesses into which the prongs may be frictionally coupled; and the filter cartridge is cylindrical in shape and in size to be concealed within the handle of the dental syringe.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a perspective view of a dental syringe with which the filter cartridge of this invention may be used;

FIG. 2 is a longitudinal cross section taken at 2—2 of FIG. 1;

FIG. 3 is a side elevational view of the filter cartridge of this invention;

FIG. 4 is a bottom plan view of the filter cartridge of this invention;

FIG. 5 is a top plan view of the filter cartridge of this invention;

DETAILED DESCRIPTION OF THE INVENTION

Figure 6:
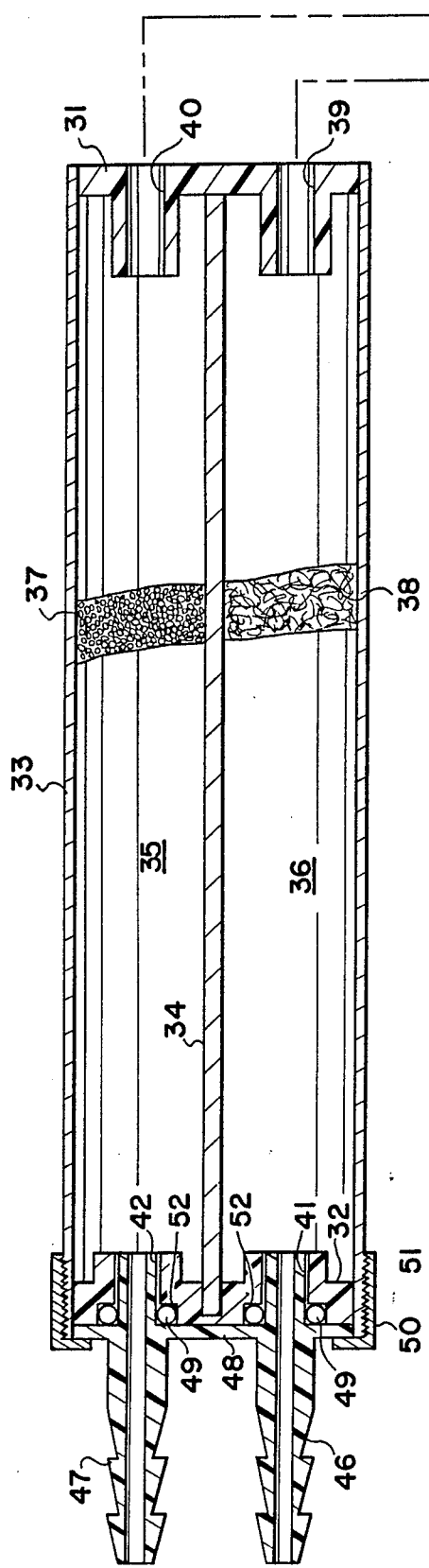
FIG. 6 is a cross sectional view taken at 6—6 of FIG. 4.

This invention may best be understood with respect to its many novel features by reference to the attached drawings.

FIG. 1 shows a modern dental syringe including a head 20, an elongated spout or nozzle 21, and a handle 22. By pressing one of buttons 23, a thin stream of water is ejected out the end of nozzle 21. By priming the other button 23, a thin stream of compressed air is ejected out the end of nozzle 21. In the prior art a flexible hose containing two independent conduits was connected to rigid conduits in head 20 leading to nozzle 21.

In accordance with the present invention a filter cartridge is provided that will fit inside handle 22 with one end of the cartridge connected to the twin conduit flexible hose 43 and the other end of the cartridge connected to the two rigid conduits in head 20. The cartridge serves to filter both the water and the air, but in separate filters, as they pass from the conduits in flexible hose 43 to nozzle 21.

In FIG. 2 there is shown the general arrangement of the filter cartridge in the dental syringe. The cartridge preferably is a cylindrical member having a side wall 33, a forward wall 31, and a rearward wall 32. A longitudinal wall 34 divides the internal space of the cartridge into two semicylindrical spaces 35 and 36. Semicylindrical space 35 is filled with water filtering material, a particularly desirable one being activated charcoal particles. Semicylindrical space 36 is filled with air filtering material, a particularly desirable one being a compacted fibrous mass such as cotton fleece. It is of course, not critical that the filter cartridge be cylindrical; it can be any shape or size but in the interests of utilizing available space to the fullest in a hollow cylindrical handle, the cartridge should conform reasonably closely to the internal space of handle 22.

In the syringe shown in FIG. 2, handle 22 is a tubular member tapering slightly from a large end joining head 20 by screw threads to a smaller end through which hose 43 is admitted. The filter cartridge for this syringe preferably is cylindrical, preferably without any tapering, so that as handle 22 is screwed onto head 20 it will contact the filter cartridge near rearward wall 32 and urge the cartridge forward toward head 20 and will not permit the cartridge from sliding out of handle 22 rearwardly.

Head 20 contains two rigid conduits, 24 for water, and 25 for air in the plug end of head 20 which joins with handle 22 by way of screw threads 26. The rearward ends of conduits 24 and 25 terminate in tapped holes into which tubular barbed prongs 28 and 29 are fastened by threaded shanks 27 on prongs 28 and 29.

The filter cartridge has in its forward wall 31 two spaced passageways positioned and sized to receive prongs 28 and 29 inserted therein in a male-female coupling. Prong 28 is coupled to water exit passageway 40, and prong 29 is coupled to air exit passageway 41.

Figure 7:
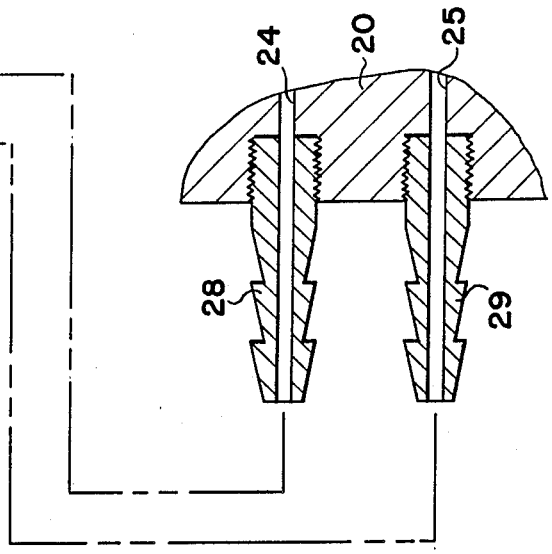
FIG. 7 is a cross sectional view of an alternate embodiment for the features shown in FIG. 6.

An alternate embodiment is shown in FIG. 7 where flanged nipples 54 are screwed into head 20 and are attached to exit passageways 39 and 40 by sliding together and pressed against o-rings 55. The pressure applied in screwing handle 22 onto head 20 supplies the pressure to seal o-rings 55 tightly against forward wall 31. These couplings and the details of the filter cartridge can be seen in FIGS. 3–7.

At the opposite end of the filter cartridge is rearward wall 32 and entrance passageways 41 and 42 which are coupled to flexible hose 43. Conduit 45 of hose 43 carries water into the filter cartridge and is, therefore, coupled to entrance passageway 42 leading to semicylindrical space 35 containing water filtering material. Similarly, conduit 44 carries compressed air and is, therefore, coupled to entrance passageway 41 leading to space 36 filled with air filtering material.

The coupling means at rearward wall 32 includes tubular barbed prongs 46 and 47, pressure plate 48, and o-rings 49 engaged together in passageways 41 and 42 to provide tight seals to prevent any leakage of water or air at the connection. Barbed prong 46 is inserted into the air conduit 44 of flexible hose 43, and barbed prong 47 is inserted into the water conduit 45 of flexible hose 43. Preferably, barbed prongs 46 and 47 and pressure plate 48 are all one piece, preferably of plastic. The shanks of prongs 46 and 47 slide into passageways 42 and 41, respectively, which are fashioned with counterbores 52 to contain o-rings 49 that fit snugly around the shanks of prongs 46 and 47. The outside of wall 33 contains external screw threads 51 to engage with ring cap 50. As ring cap 50 is screwed tightly onto the filter cartridge it presses plate 48 against o-rings 49 which flex outwardly to make a water-proof and air-proof seal between the shanks of prongs 46 and 47 and respective passageways 41 and 42. Prongs 46 and 47 may be separate from pressure plate 48, may be connectable to plate 48 by screw threads, or through other feasible connecting means.

A preferred feature is for handle 22 to be fitted with a window 53 of glass or plastic to permit visual inspection of the filter cartridge, particularly of semicylindrical space 36 containing the air filter, so as to provide an easy way to tell when a new cartridge is needed. It is, of course, possible to have window 53 extend circumferentially so as to view both spaces 35 and 36. Indexing of the proper orientation of the filter cartridge can be used to be sure that window 53 permits inspection of either or both of spaces 35 and 36 and their respective filtering materials.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. In a dental syringe for selectively directing streams of air or water into a patient's mouth, a disposable filter cartridge having separate filters for air and for water comprising:

(a) an elongated cartridge body having a forward wall, a rearward wall, and a side wall enclosing an internal space divided into two longitudinal half spaces by an internal axial wall extending from said forward wall to said rearward wall; the first of said longitudinal spaces being filled with water filtering material and the second of said spaces being filled with air filtering material; an entrance passageway for water through said rearward wall into said first space, an entrance passageway for air through said rearward wall into said second space; an exit passageway from said first space through said forward wall to a coupling means with said syringe; and exit passageway from said second space through said forward wall to a coupling means with said syringe; and means to couple said entrance passageways to separate sources of pressurized air and pressurized water.

2. The filter cartridge of claim 1 wherein said water filtering material is granular activated carbon.

3. The filter cartridge of claim 1 wherein said air filtering material is a compact mass of fibrous material.

4. The filter cartridge of claim 3 wherein said mass of fibrous material is cotton fleece.

5. The filter cartridge of claim 1 wherein said means to couple said entrance passageways to separate sources of pressurized air and pressurized water includes a tubular barbed prong projecting outwardly from each said passageway, respectively, coupled to a flexible hose conduit for air and a flexible hose conduit for water.

6. The filter cartridge of claim 1 wherein said coupling means with said syringe including a tubular barbed prong for air projecting outwardly from said syringe and coupleable to said exit passageway for air by frictional engagement of said prong in said exit passageway; and a tubular barbed prong for water projecting outwardly from said syringe and coupleable to said exit passageway for water by frictional engagement of said prong for water in said exit passageway for water.

7. The filter cartridge of claim 1 which is cylindrical in shape with external screw threads around the outside surface thereof adjacent said rearward wall; a pressure plate substantially coextensive with and separate from said rearward wall and having an outside planar surface and an inside planar surface; two tubular barbed prongs projecting outwardly from said outside surface, each said prong having a tubular shank projecting outwardly from said inside surface, adapted to slide into said entrance passageway in said rearward wall and defining an internal conduit through said shank and said prong; an o-ring gasket around the outside of each said tubular shank adapted to form a seal between said tubular shank and said entrance passageway; and a ring cap member having internal screw threads to engage said external screw threads of said cartridge; said ring cap member structured and adapted to compress said plate against said o-rings, which, in turn, are compressed against said tubular shank and against said entrance passageway.

8. The filter cartridge of claim 1 for use in said dental syringe comprising a head, a tubular nozzle, and a hollow tubular handle attachable to said head by mutually engagable screw threads on said head and said handle, said filter cartridge being of a size and shape to be positioned completely inside said handle.

9. The filter cartridge of claim 1 wherein each of said entrance and exit passageways is a short tubular member extending through said rearward and said forward walls, respectively.

* * * * *